United States Patent [19]

Fisher

[11] Patent Number: 5,558,630
[45] Date of Patent: Sep. 24, 1996

[54] INTRASCLERAL IMPLANT AND METHOD FOR THE REGULATION OF INTRAOCULAR PRESSURE

[76] Inventor: Bret L. Fisher, 224 S. Cove La., Panama City, Fla. 32401

[21] Appl. No.: 366,503

[22] Filed: Dec. 30, 1994

[51] Int. Cl.$^6$ .............................. A61M 5/00; A61F 2/14
[52] U.S. Cl. ...................................... 604/8; 623/4
[58] Field of Search .............................. 623/4; 604/289, 604/294, 8–10

[56] References Cited

U.S. PATENT DOCUMENTS

| | | | |
|---|---|---|---|
| 4,402,681 | 9/1983 | Haas et al. | 604/9 |
| 4,634,418 | 1/1987 | Binder | 604/8 |
| 4,750,901 | 6/1988 | Molteno | 604/8 |
| 4,886,488 | 12/1989 | White | 604/9 |
| 5,041,081 | 8/1991 | Odrich | 604/9 |
| 5,073,163 | 12/1991 | Lippman | 604/9 |
| 5,171,213 | 12/1992 | Price, Jr. | 604/9 |
| 5,178,604 | 1/1993 | Baerveldt et al. | 604/8 |
| 5,370,607 | 12/1994 | Memmen | 604/8 |

*Primary Examiner*—Mary Beth Jones
*Attorney, Agent, or Firm*—Longacre & White

[57] ABSTRACT

A tubular conduit style implant device for the regulation of intraocular pressure is described. The device is generally funnel shaped and enlarges from its forward end, for implanting in the anterior chamber of an eye, to its rearward end, for implanting in the sclera. The tubular body of the device includes laterally extending appendages adapted to stabilize the implant from rocking in position. In addition, the forward end of the device includes both a positioning ridge, to space the device from an inner surface of the eye, and an oppositely positioned retention flange to prevent migration of the implant from the anterior chamber. The rearward end of the device positioned within the sclera includes fluid passageways for controlling fluid outflow from the interior of the eye.

7 Claims, 3 Drawing Sheets

5,558,630

1

INTRASCLERAL IMPLANT AND METHOD FOR THE REGULATION OF INTRAOCULAR PRESSURE

FIELD OF THE INVENTION

This invention relates to ocular implants and associated methods useful for the reduction of intraocular pressure.

BACKGROUND OF THE INVENTION

The surgical treatment of glaucoma remains a challenging subject. Patients with progressive visual field and optic nerve damage, despite maximal tolerated medical therapy and laser treatment, have traditionally been offered surgical approaches to the regulation of their intraocular pressure only as a last resort. For the most part, this was because of the high complication and failure rates of surgical approaches and the consequent increased risk-to-benefit ratio associated with surgery. Recently, the advent of anti-metabolite agents has increased the effectiveness of primary surgical approaches, but has introduced a new set of potential complications and attendant risks.

Current implants used for the regulation of intraocular pressure are associated with a number of problems. They are generally difficult to implant, requiring a long learning curve for a typical surgeon to become comfortable with their use. Current designs are also cumbersome, often requiring several different procedures or surgeries in order to insure proper functioning of the implant. Frequent medical complications are experienced with all current designs of ocular implants for the regulation of intraocular pressure. Currently available implants are also poorly, if at all, adjustable in the amount of filtration which may be achieved through their use.

For these and many other reasons, many ophthalmologists remain disillusioned about the prospect of regulating intraocular pressure through the use of a surgical implant.

Examples of prior ocular implants useful for reducing intraocular pressure include those disclosed in U.S. Pat. Nos. 4,402,681, 5,178,604, 5,041,081, 5,171,213, 4,634,418, 4,886,488, 5,041,081.

SUMMARY OF THE INVENTION

The object of the present invention is to provide a simple, effective, permanently implantable device and method for the regulation of intraocular pressure. A device according to the present invention should be easy to learn to use, easy to implant, made of readily available materials, and effective in achieving a wide and predictable range of effect on intraocular pressure.

A device according to the present invention includes a thin, hollow, wedge shaped funnel type device made of flexible or semi-rigid biologically inert material which, when implanted intrasclerally, creates a known resistance to the outflow of fluid from the anterior chamber into the sclera. The resistance, or fluid pressure gradient through the conduit, can be varied according to the number and sizing of a grid of fluid outflow passages located in the rearward plate portion of the conduit which covers the larger and exit end of the conduit. The implant is stabilized in position by several appending elements positioned along the side portions of the conduit and at each end thereof. The object of the stabilizing elements is to secure the implant in position, resist displacement owing to patient eye manipulation, and to reduce the likelihood of unintended contact with surrounding eye tissue. The stabilizing elements can comprise extended rib elements along the sides of the conduit, flange elements positioned around the fluid entrance to the conduit, and a trailing flange appended to the back end fluid exit of the conduit. The trailing flange may also include holes therein for purposes of suturing or otherwise positively associating the implant conduit with surrounding eye tissue.

The implant is sized suitably for placement within a scleral pocket or tunnel type incision which accesses the anterior chamber of the eye. Owing to the location of the implant conduit, no interference with surgical technique should likely result when used in combination with a cataract procedure wherein a scleral tunnel incision is used.

The intrascleral location of the device should lessen the chance of infection, extrusion, discomfort, or failure due to formation of scar tissue. Filtration of fluid from the anterior chamber into the sclera also represents a more physiologic means by which to lower intraocular pressure, and is an accepted pathway by which many pharmacologic agents currently in use are thought to lower pressure.

An implant according to the present invention contains no moving parts, valves, tubes or other features prone to failure. Its design would facilitate production as a single piece, without the disadvantage of multi-piece assembly. The proposed device would offer a realistic means for controlling the resistance to outflow, and therefore the intraocular pressure, by varying the number and size of fenestrations in the rearward portions of the implant. In addition, its shape and structure lend to ease in implantation, obviating the need for extended training in its use.

Other advantages and features of the present invention will be apparent from a review of the following specification, drawings, and claims which form a part thereof.

BRIEF DESCRIPTION OF THE DRAWINGS

FIG. 3b is an enlarged detail view of the implant according to the present invention as positioned according to FIG. 3a.

DETAILED DESCRIPTION OF THE PREFERRED EMBODIMENTS

Figure 1:
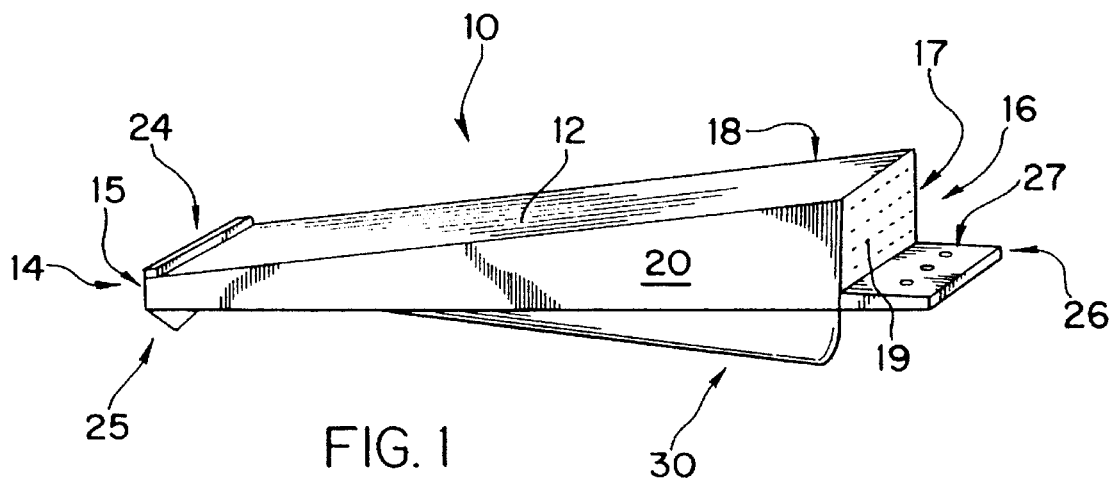
FIG. 1 a perspective view of an implant according to the present invention.
Figure 2:
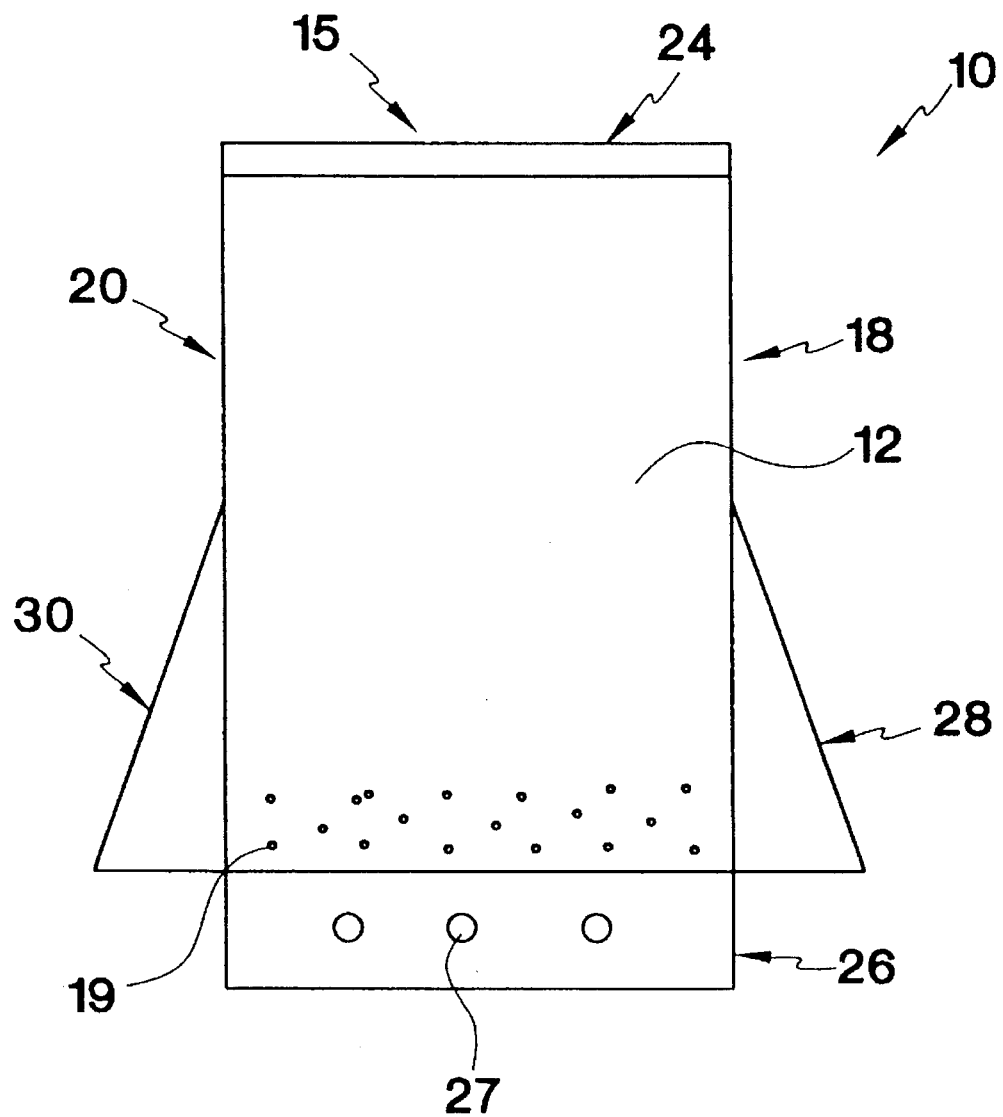
FIG. 2 is a top plan view of an implant according to the present invention; and, FIG. 3a is a partial section view of an eye having an implant according to the present invention located therein.

The implant device according to the present invention shall described with reference to the drawing FIGS. 1–3.

Figure 4:
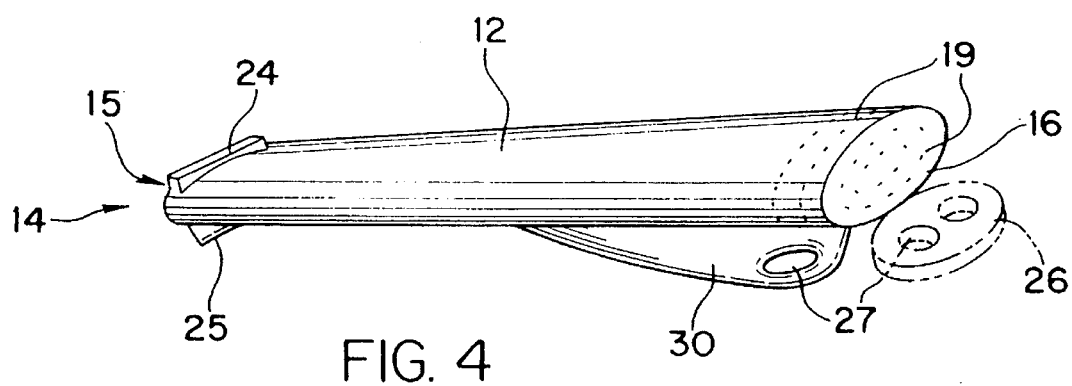
FIG. 4 is a perspective view of an alternative embodiment of an implant according to the present invention having a non-rectangular shape.

An implant 10 according to the present invention comprises an intraocular pressure regulation device which is adapted for insertion into a scleral tunnel type of incision. The implant 10 includes a tubular body 12 having a forward end 14 for insertion into the anterior chamber of an eye and a rearward end 16 for insertion intrasclerally. The tubular body 12 is generally conduit shaped and in this embodiment is shown to be approximately rectangular in cross section. Other cross sectional shapes may be electively adapted, see FIG. 4, for the conduit as long as the shape in combination with laterally appended stability elements resists displacement of the implant following insertion.

In the embodiment shown, the tubular body 12 includes side portions 18 right and 20 left. These respective side portions 18 and 20 include stability flanges 28 and 30 for preventing rocking of the implant within its scleral tunnel implantation site. In addition to the side stability flanges 28 and 30 the tubular body 12 also includes stability elements appended to the forward end 14 and rearward end 16 thereof. At the forward end 14 the fluid entrance 15 includes a positioning ridge 24 and a retention flange 25. The positioning ridge 24 is adapted to keep the conduit forward end 14 from contacting the corneal endothelium once the implant is in position. The positioning ridge 24 reduces contact with the corneal endothelium to a line of contact along the ridge and, since the ridge is finished to a smooth non-tissue irritating surface, no damage to the corneal endothelium should result.

The retention flange 25 is positioned to be on a side of the conduit opposite the positioning ridge 24 and potential endothelium contact. The retention flange 25 is shaped to resist extraction of the conduit from the anterior chamber of the eye and is shaped to engage the internal ledge of the entrance into the anterior chamber. For example, in a tunnel type incision which terminates in an anterior chamber entrance including an internal corneal lip or valve, the retention flange 25 is shaped to include a rearward slant for riding against the lip and resisting outward migration of the implant 10.

The implant 10 overall shape is funnel like with an enlarging of the funnel proceeding from the forward fluid entrance 15 to a rearward end 16 and flow plate 17. The flow plate 17 covers the rearward end 16 of the tubular conduit body 12 and prevents unchecked fluid outflow from the anterior chamber location of the forward end 14 of the implant 10. The flow plate 17 includes fluid passages 19 therethrough spaced in an approximate grid pattern. The sizing and number of fluid passages 19 and in flow plate 17 is elective and can be varied according to the necessary outflow required from the conduit to relieve excessive intraocular pressure. The selected rate of flow is dependant upon the production of excess fluid within the eye of a treated patient. Where one patient may have a modest fluid outflow need, another patient may have a greater need. An implant according to the present invention could be provided at varied rates of fluid flow for measured intraocular pressures. In this way, a treating physician could match the tested flow rate of an implant 10 to the particular need of a patient. These tested rates could be expressed in the form of pressure gradients of Hg mm. required for fluid to pass through the implant. For example versions of the implant could be offered in 5 mm, 10 mm, and 15 mm pressure gradients.

The rearward end 16 of the tubular body 12 also includes a back flange 26 which may include positioning holes 27. The back flange 26 allows for placement of the implant using instruments and with the provision of holes 27 allows the use of sutures to positively locate the implant 10 within the scleral layers.

As previously recited, the overall shape of the conduit, whether rectangular or other shape in cross section, is generally funnel shaped and enlarges along its length from the forward end 14 to the rearward end 16. The embodiment shown illustrates this enlargement in one cross sectional dimension of the conduit, i.e., vertical, but this enlargement may occur in the opposed cross sectional direction, i.e., width, or in both. A partial object of the enlarging shape is to increase the exposed surface of the flow plate 17 to surrounding scleral tissue. While it is known that this tissue can scar and become less absorbent as a result, if proportionately more tissue is exposed to a given amount of the passing fluid, more fluid should be absorbed. In addition, as an additional means of increasing exposed surface are, the fluid passageways 19 may also be included along the generally rearwardly located flanks of the tubular body 12.

The implant is made from any biologically inert and biocompatible material having the necessary characteristics of semi-rigidity and flexibility. Various medically suitable acrylics and other plastics are considered appropriate. The sizing of the implant can be varied, for the embodiment shown, an overall length in the range of 3 mm, with a width of 2 mm, and a depth at the forward end of 0.25 mm, and a depth at the rearward end of 0.5 mm. The rearward and side portion appended stability, securement, and manipulation elements are sized in the range of 0.5 mm. in lateral extent. The holes 27 provided in the rearward or back flange 27 can be expanded for purposes of access to form 0.25 mm dimension windows to enable easier suture access and passage. The finish on the device 10 should be to the standard for ophthalmic devices and in no instance should include edges or surfaces which would create irritation to the surrounding tissue or enable displacement through adjacent tissue.

This device 10 is designed to be implanted through a self-sealing scleral tunnel incision, identical to the type widely used by many cataract surgeons at present. Because of this, it should be readily accepted by general ophthalmologists, who could incorporate it easily into already established surgical techniques. It could also be used at the time of cataract surgery for combined cataract and glaucoma procedures without significantly lengthening or complicating the primary cataract procedure. It would thus present an attractive and cost-effective technological alternative for the high-volume cataract surgeon, who otherwise would be reluctant to use any of the more cumbersome implants previously known.

Figure 3A:
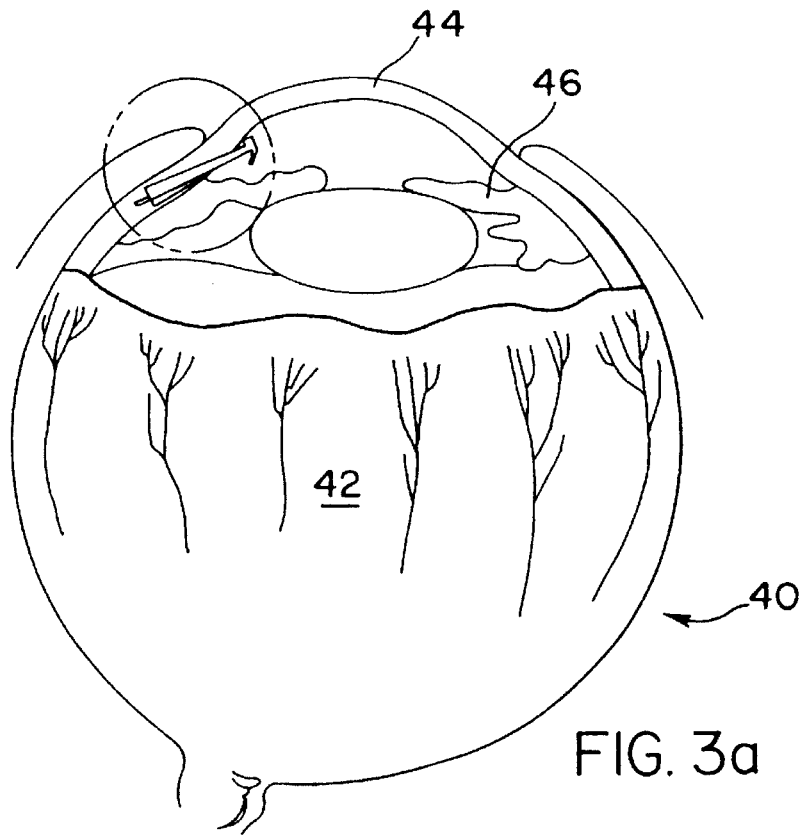
Figure 3B:
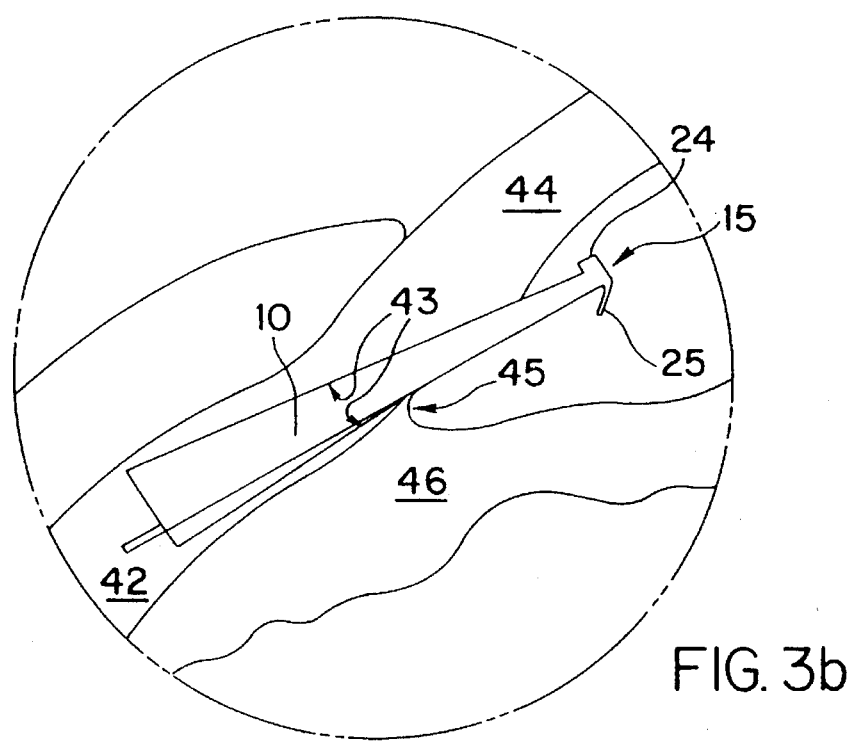

FIG. 3 shows an eye 40 having an implant 10 according to the present invention implanted within the sclera 42. A forward end 14 of the implant 10 extends into the anterior chamber 41 of the eye 40 at a position anterior to the iris 46 and through clear cornea 44. The tunnel incision 43 shown terminates in a corneal valve type entrance 45 to the anterior chamber 41. The incision 43 closes behind the implant 10 following surgery and the surrounding scleral tissue 42 absorbs intraocular fluid passing through the implant 10.

The method of implantation would include accessing the anterior chamber of an eye using a scleral tunnel method of incision. The tunnel should commence at a scleral groove of suitable partial scleral depth and geometry followed by a scleral dissection to clear cornea followed by a bevelled entrance into the anterior chamber at a location anterior to the iris. If no other procedure, such as cataract removal, is being performed, the tunnel width should only such as to accommodate the placement of the implant device 10. For the embodiment shown herein a tunnel width of approximately 2.5 mm should suffice. The implant should be inserted through the tunnel by grasping the back flange 26 and manipulating the implant into position. The tubular body should extend by its forward end 14 into the anterior chamber such that the retention flange is located inside the anterior chamber and is able to engage the interior ledge of the cornea created by the internal entrance into the anterior chamber. The implant is then electively sutured in place through the holes provided in the back flange and the scleral flap is replaced to cover the implant. If the scleral tunnel is constructed in a manner consistent with a self-sealing method, no sutures to close the wound should be required.

The foregoing specification describes various embodiments of the present invention, but in no respect limits the scope of the invention or what others skilled in the art may take from this disclosure.

What I claim is:

1. An intrascleral implant for implanting within the eye and for reducing intraocular fluid pressure, comprising:

a tubular body having a forward end, adapted for placement within an anterior chamber of an eye, and a rearward end, adapted for placement within the sclera of an eye, said tubular body being funnel shaped and enlarging in cross-section along said tubular body in a direction from said forward end to said rearward end, said rearward end including fluid passageways to limit and control a flow of intraocular fluid through said tubular body from said anterior chamber to said sclera, said tubular body further including side portions and at least one implant stability flange appending therefrom and adapted to stabilize said tubular body against said sclera, said tubular body further including a positioning ridge located on said forward end, said positioning ridge being smoothly finished and adapted to space said tubular body from an inner surface of said anterior chamber.

2. An implant as recited in claim 1, further comprising:

a retention flange located on said forward end and positioned opposite from said positioning ridge, said retention flange being adapted to engage an inner surface of said eye and resist migration of said implant from said anterior chamber.

3. An implant as recited in claim 1, further comprising:

a back flange appended to and extending from said rearward end, said back flange being adapted to contact said sclera and attach thereto by attachment means.

4. An implant as recited in claim 1, wherein:

said fluid passageways are provided in longitudinal side portions of said tubular body in a region of said tubular body proximate said rearward end.

5. An implant as recited in claim 1, wherein:

a cross section through said tubular body at a mid-point thereof has an approximately rectangular shape.

6. An implant as recited in claim 1, wherein:

a cross section through said tubular body at a mid-point thereof has a curving shape.

7. A method of regulating intraocular fluid pressure comprising the steps of:

providing an incision into an eye, said incision commencing at a partial depth scleral groove and extending through scleral dissection to a clear cornea entrance into the anterior chamber of said eye;

placing an implant in said incision, said implant having a tubular body having a forward end, adapted for placement within said anterior chamber, and a rearward end, adapted for placement within said sclera, said tubular body being funnel shaped and enlarging longitudinally along said tubular body in a direction from said forward end to said rearward end, said rearward end including fluid passageways to limit and control a flow of intraocular fluid through said tubular body from said anterior chamber to said sclera, said tubular body further including side portions, stabilizing said implant against said sclera by providing at least one implant stability flange appending from said tubular body, said placing step including extending said forward end into said anterior chamber to enable intraocular fluid flow from said anterior chamber into said tubular body, spacing said tubular body from an inner surface of said anterior chamber by providing a positioning ridge on said forward end of said tubular body, said positioning ridge being smoothly finished; and, electively suturing said implant in place to said sclera at said rearward end.

* * * * *